United States Patent
Swan et al.

(10) Patent No.: US 12,089,986 B2
(45) Date of Patent: Sep. 17, 2024

(54) ON-SCREEN MARKERS FOR OUT-OF-PLANE NEEDLE GUIDANCE

(71) Applicant: FUJIFILM SonoSite, Inc., Bothell, WA (US)

(72) Inventors: Wendy Swan, Lake Forest Park, WA (US); Keith Williams, Seattle, WA (US); Andrew Lundberg, Woodinville, WA (US)

(73) Assignee: FUJIFILM SonoSite, Inc., Bothell, WA (US)

( * ) Notice: Subject to any disclaimer, the term of this patent is extended or adjusted under 35 U.S.C. 154(b) by 0 days.

(21) Appl. No.: 18/351,221

(22) Filed: Jul. 12, 2023

(65) Prior Publication Data

US 2023/0346336 A1    Nov. 2, 2023

Related U.S. Application Data

(63) Continuation of application No. 16/440,676, filed on Jun. 13, 2019, now Pat. No. 11,730,443.

(51) Int. Cl.
*A61B 8/08* (2006.01)
*A61B 8/12* (2006.01)
*A61B 34/20* (2016.01)

(52) U.S. Cl.
CPC .............. *A61B 8/0841* (2013.01); *A61B 8/12* (2013.01); *A61B 34/20* (2016.02); *A61B 2034/2063* (2016.02)

(58) Field of Classification Search
CPC .... A61B 2017/3413; A61B 2034/2063; A61B 2090/378; A61B 34/20; A61B 34/25;
(Continued)

(56) References Cited

U.S. PATENT DOCUMENTS 6,733,458 B1   5/2004   Steins et al.
9,492,097 B2   11/2016   Wilkes et al.
(Continued)

FOREIGN PATENT DOCUMENTS

JP   2009125280   6/2009
JP   2018023610   2/2018
(Continued)

OTHER PUBLICATIONS

"Extended European Search Report", EP Application No. 20823335.3, Jun. 2, 2023, 9 pages.
(Continued)

*Primary Examiner* — Joseph M Santos Rodriguez
*Assistant Examiner* — Maria Christina Talty
(74) *Attorney, Agent, or Firm* — Colby Nipper PLLC

(57) ABSTRACT

An ultrasound imaging system including an image processor configured to receive input data for capturing ultrasound images of a region of interest. The ultrasound images are taken along a first plane; and the input data further includes an indication that a needle will be inserted into the region of interest. The system can capture a plurality of ultrasound images of the region of interest along the first plane. The system can determine one or more high-confidence areas of the region of interest where the needle will intersect the first plane. Each high-confidence area is based on a probability that the needle will intersect the first plane at any portion of the high-confidence area; and display one or more on-screen markers corresponding to the one or more high-confidence areas in conjunction with the plurality of ultrasound images on the display.

20 Claims, 9 Drawing Sheets

(58) Field of Classification Search
CPC ......... A61B 8/0841; A61B 8/12; A61B 8/145;
A61B 8/461; A61B 8/463; A61B 8/469;
A61B 8/483; A61B 8/5223
See application file for complete search history.

(56) References Cited

U.S. PATENT DOCUMENTS

| | | |
|---|---|---|
| 9,554,716 B2 | 1/2017 | Burnside et al. |
| 11,730,443 B2 | 8/2023 | Swan et al. |
| 2005/0059883 A1 | 3/2005 | Peterson |
| 2007/0112272 A1 | 5/2007 | Park et al. |
| 2010/0298705 A1 | 11/2010 | Pelissier et al. |
| 2011/0245659 A1 | 10/2011 | Ma et al. |
| 2012/0059260 A1 | 3/2012 | Robinson |
| 2012/0099770 A1 | 4/2012 | Cagnan et al. |
| 2016/0000399 A1 | 1/2016 | Halmann et al. |
| 2016/0324501 A1 | 11/2016 | Vignon et al. |
| 2016/0374644 A1 | 12/2016 | Mauldin et al. |
| 2017/0065352 A1 | 3/2017 | Razzaque et al. |
| 2017/0095226 A1 | 4/2017 | Tanaka et al. |
| 2021/0378758 A1 | 12/2021 | Vaidya et al. |

FOREIGN PATENT DOCUMENTS

| | | |
|---|---|---|
| WO | 2013059714 | 4/2013 |
| WO | 2020083863 | 4/2020 |

OTHER PUBLICATIONS

"Final Office Action", U.S. Appl. No. 16/440,676, filed Nov. 17, 2021, 22 pages.

"International Search Report and Written Opinion", Application No. PCT/US2020/037143, Sep. 18, 2020, 18 pages.

"Non-Final Office Action", U.S. Appl. No. 16/440,676, filed May 14, 2021, 16 pages.

"Non-Final Office Action", U.S. Appl. No. 16/440,676, filed Sep. 2, 2022, 25 pages.

"Notice of Allowance", U.S. Appl. No. 16/440,676, filed Mar. 22, 2023, 10 pages.

Kaya, Mert, et al., "Gabor Filter Based Localization of Needles in Ultrasound Guided Robotic Interventions", Oct. 2014, 6 pages.

"Foreign Office Action", JP Application No. 2021-573958, Jan. 16, 2024, 8 pages.

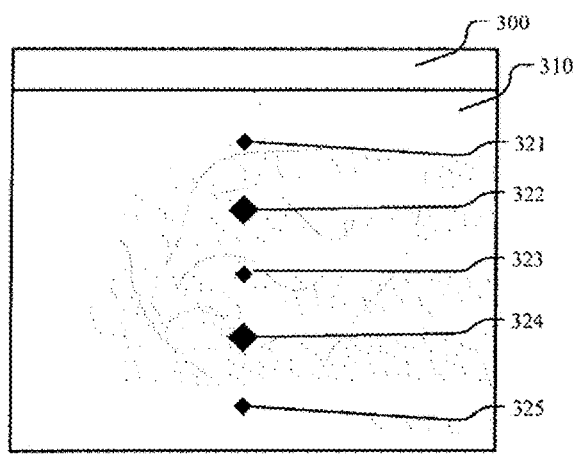 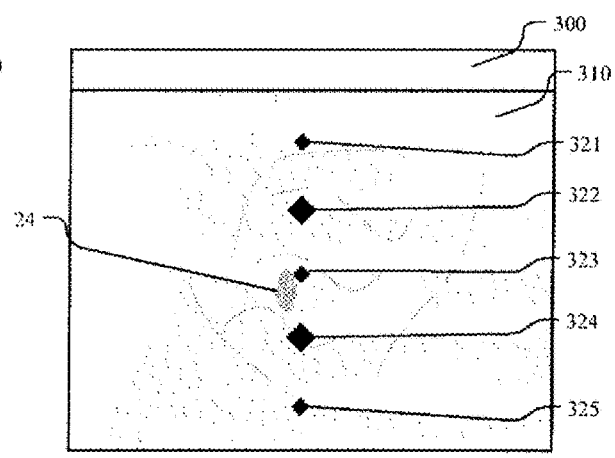
*FIG. 3A*            *FIG. 3B*

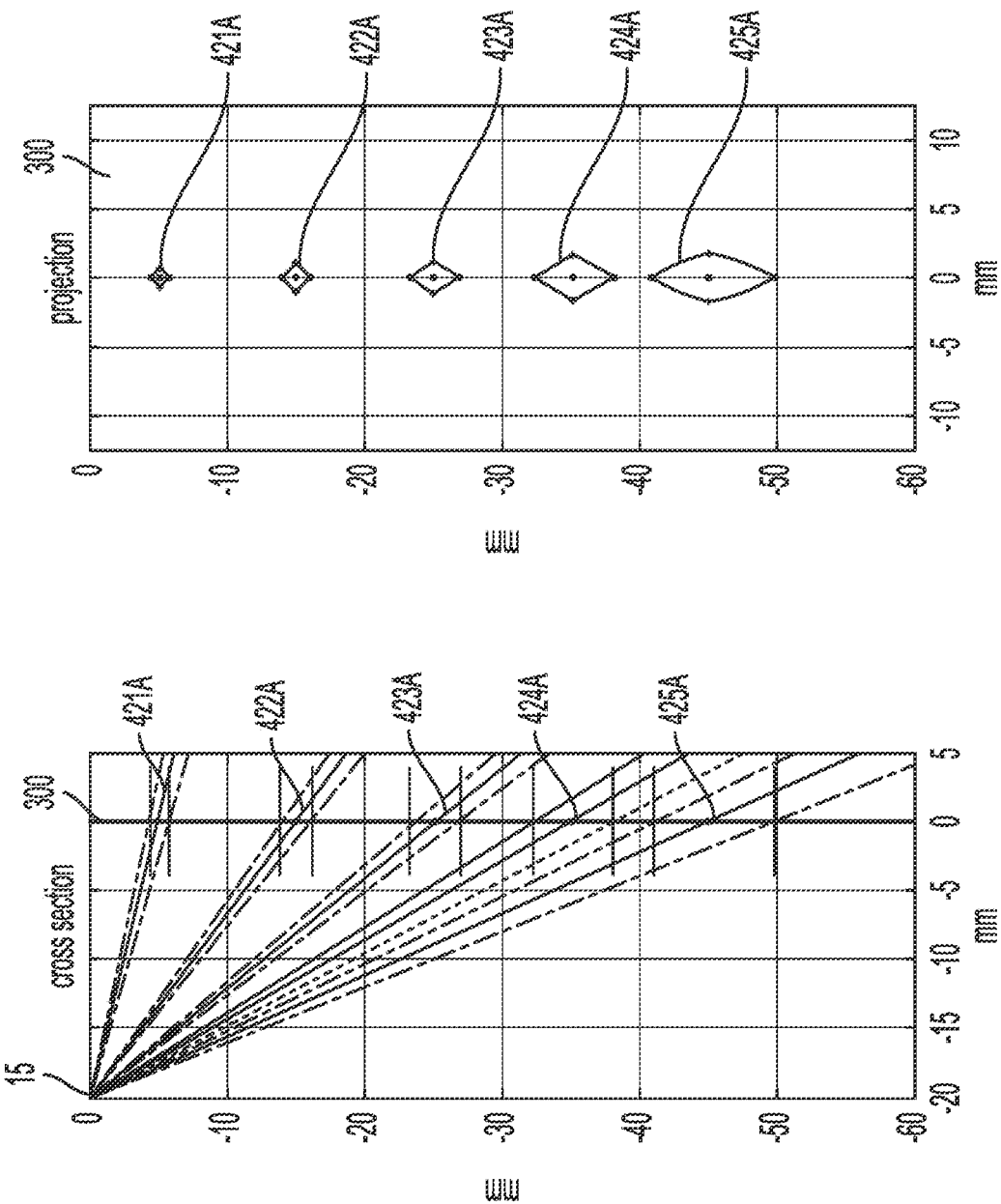

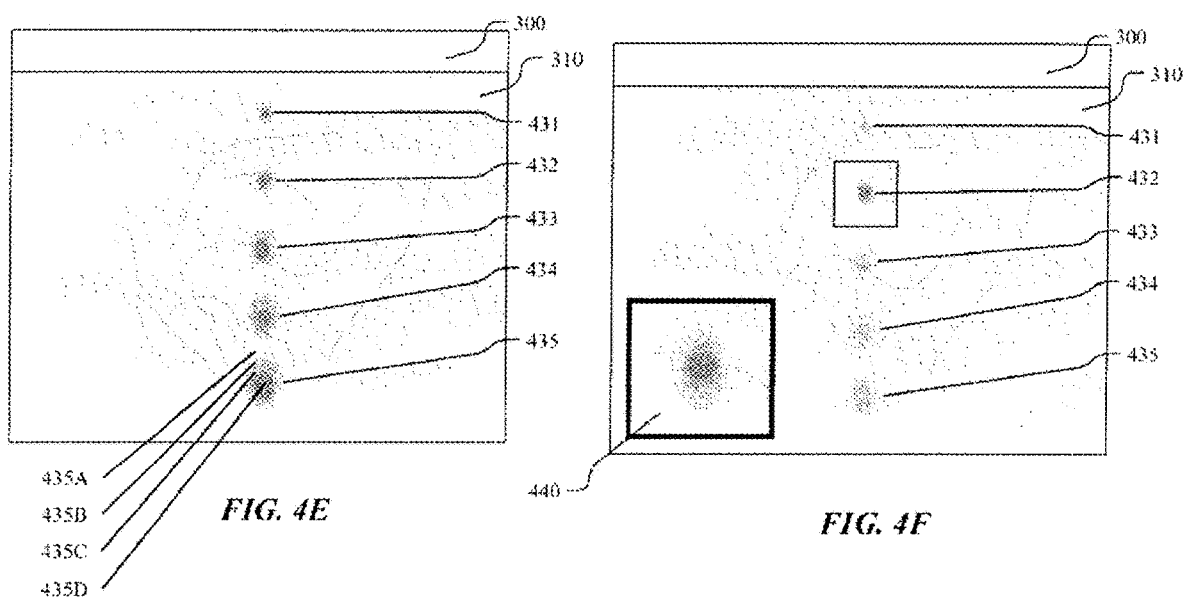

ON-SCREEN MARKERS FOR OUT-OF-PLANE NEEDLE GUIDANCE

RELATED APPLICATIONS

This application is a continuation of and claims priority to U.S. patent application Ser. No. 16/440,676, filed Jun. 13, 2019, the disclosure of which is incorporated by reference herein in its entirety.

TECHNICAL FIELD

The disclosed technology relates to ultrasound imaging systems and in particular to ultrasound imaging systems for depicting the location of interventional instruments such as needles within an anatomic structure.

BACKGROUND

Ultrasound imaging is becoming increasingly accepted as the standard of care to be used when guiding an interventional instrument such as a needle to a desired location within a body. One common use for this procedure is during the application of anesthesia, whereby a physician or a medical technician ("operator") views an ultrasound image to help guide a needle to a desired region of interest. The relative positions of the displayed ultrasound image to the needle may be one of two configurations: (1) "in-plane," where the longitudinal axis of the needle is within the plane of the ultrasound image (i.e. the needle appears as a line-like structure); or (2) "out-of-plane," where the needle is perpendicular to the plane of the ultrasound image (i.e., the needle appears as a dot). A mechanical needle guide is used to fix the angle of the needle relative to the ultrasound transducer (and hence the skinline) so that its trajectory is predictable. Consequently, the bounds of the expected needle intersection with the plane of the ultrasound image (accounting for the mechanical variability of a needle guide) may be delineated by parallel or slightly diverging lines for in-plane applications and a circle or ellipse for out-of-plane applications. In particular embodiments, an out-of-plane needle guidance is desirable so that the operator may view an anatomic structure, such as a blood vessel, relative to the position of the needle.

In particular embodiments, the out-of-plane needle guidance only depicts the location of the needle at the point where it intersects the plane of the image, as discussed above. In particular embodiments, the operator may not be able to determine the location of the needle relative to the anatomic structures of interest until the needle intersects the plane; this means that for some time after the needle is initially inserted, the operator is unable to predict with certainty where the needle will intersect the plane. In particular embodiments, ideally, the needle would appear on the ultrasound image as it reaches the anatomic feature of interest. As an example and not by way of limitation, the operator may see the needle on the ultrasound image approximately as the tip of the needle reaches a targeted blood vessel.

To better ensure placement of the needle for out-of-plane guidance, fixed-angle needle guides are used. These guides are affixed to the ultrasound transducer (for example, by a bracket), and hold the needle at a specific position and angle relative to the ultrasound transducer, meaning that the position of the needle relative to the ultrasound image (and therefore, to the anatomic feature of interest) is more accurately known, reducing the chances of operator error in placement of the needle. However, there are still other factors that reduce the accuracy of the needle placement in the out-of-plane guidance. For example and not by way of limitation, mechanical play between the needle and guide, the fit of the bracket on the housing of the ultrasound transducer, the alignment of the ultrasound transducer array within the transducer housing, the tissue density of the anatomic feature, thickness and profile of the ultrasound imaging plane, and deflection of the needle shaft as it progresses through to the target feature may all affect the precise location of the needle when it intersects the plane of the ultrasound image.

In particular embodiments, based on the preset angle and type of needle, an ultrasound imaging system may be able to predict where the needle will intersect the imaging plane and project an on-screen marker or other indicator on the ultrasound image to notify the user. However, even this on-screen marker may be imprecise due to other factors impacting the needle's trajectory, and may not provide a complete indicator of how likely it is that the needle will intersect the image at the indicated location.

BRIEF DESCRIPTION OF THE DRAWINGS

FIGS. 3A-3B depict an example of a set of on-screen depth markers indicating various depths through the plane of the ultrasound image.

FIGS. 4A-B depicts the relationship between needle insertion angle and an ultrasound image plane.

FIGS. 4C-4H depict example diagrams of on-screen markers corresponding with high-confidence areas.

DETAILED DESCRIPTION

As will be explained in further detail below, the disclosed technology relates to improvements in ultrasound imaging systems and in particular to an ultrasound imaging system that is configured to calculate and display on-screen markers on an ultrasound image that correspond to a probability that an out-of-plane needle insertion will intersect the plane of the ultrasound image at the location of the marker. While this disclosure uses the term "needle" to refer to the object that is being inserted from an out-of-plane direction, which may include but is not limited to injection needles, biopsy needles, needles for suturing tissue, and needles for withdrawing fluids (e.g. amniocentesis), other devices such robotic surgical instruments, catheters, guidewires or other invasive medical instruments may also be imaged.

In particular embodiments, an ultrasound imaging system may create and deliver a plurality of transmit ultrasound beams to a region to be imaged. As an example and not by way of limitation, the region to be imaged may be organic tissue, live animals, portions of animal or human anatomy, or any other suitable medium that can be measured via ultrasound imaging. For didactic purposes, this disclosure will refer to the region to be imaged as an anatomic structure. In particular embodiments, the ultrasound imaging system may be capable of imaging not only the targeted anatomic structure, but also other objects present within the anatomic structure, such as a needle.

Figure 1:
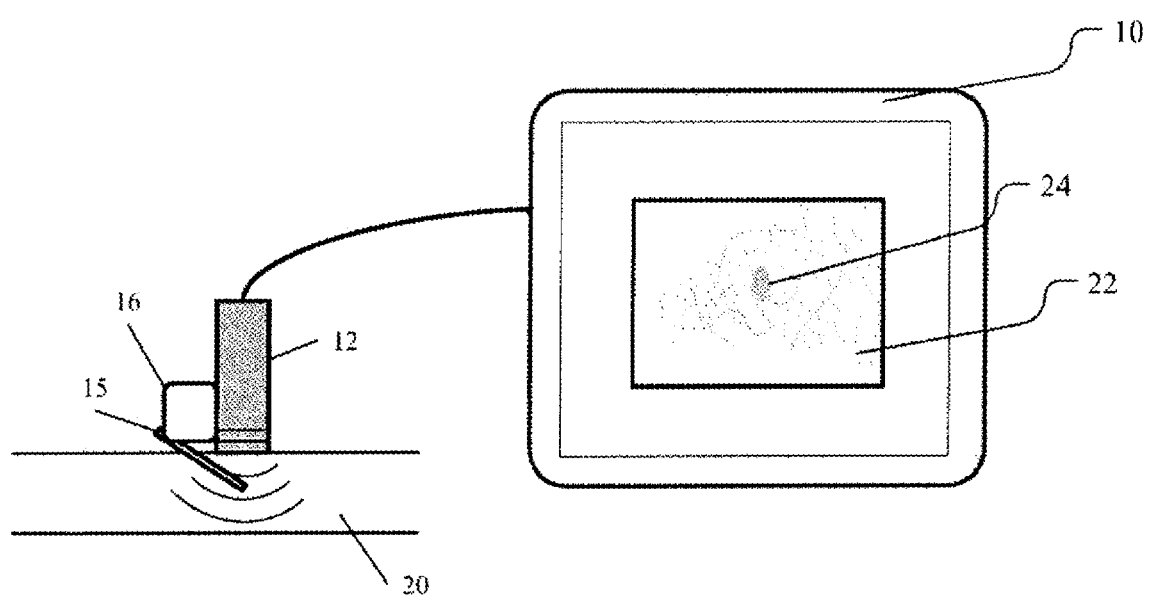
FIG. 1 depicts a simplified illustration of an example ultrasound imaging system with out-of-plane needle guidance.

FIG. 1 depicts a representative ultrasound imaging system that implements the disclosed technology for imaging the tissue of a patient, with the ability to perform out-of-plane needle guidance. In particular embodiments, an ultrasound imaging system 10 may be a hand-held, portable or cart-based system that uses a transducer 12 to transmit ultrasound signals into a region of interest and to receive the corresponding echo signals in order to produce an image of the tissue being scanned. The transducer 12 may be a one- or two-dimensional linear or curved transducer or a phased array transducer, all of which can selectively change the transmit beam angles electronically.

The ultrasound imaging system 10 may convert characteristics of the received echo signals (e.g. their amplitude, phase, power, frequency shift etc.) into data that is quantified and displayed for the user as an image. The images created may also be stored electronically for digital record keeping or transmitted via a wired or wireless communication link to another device or location. In particular embodiments, an operator may affix an out-of-plane needle guidance system 16 to the transducer 12, where the needle guidance system 16 may hold a needle 15 for insertion into the target region along a plane orthogonal to the plane being displayed for imaging. In particular embodiments, the needle guidance system 16 may allow a variety needles (e.g., gauge or length) and angles of insertion, so that the needle intersects the plane of the ultrasound image at the desired depth into the target region. The ultrasound imaging system 10 may generate a composite view 22 of the target region and the needle 24 as it intersects the plane of the target region.

In particular embodiments, a fixed-angle, out-of-plane needle guidance system 16 may be used to perform out-of-plane needle procedures. As an example and not by way of limitation, an out-of-plane needle procedure may be desirable where an operator is attempting to place a needle along a structure 20 such as a blood vessel, and an out-of-plane view would allow the operator to visualize the cross-section of the blood vessel walls as well as the needle. In particular embodiments, because the out-of-plane needle guidance system 16 is affixed to the ultrasound transducer 12, the ultrasound imaging system may be able to determine, based on factors such as the angle of the guidance system and the type of needle, where the needle will intersect the plane of the image. The ultrasound imaging system 10 can show the needle 24 in the composite view 22, as shown in FIG. 1. As will be appreciated by one of ordinary skill in the art, there may be a variety of out-of-plane needle guidance systems available for ensuring that a needle is in a fixed position relative to the ultrasound transducer.

In particular embodiments, the out-of-plane needle guidance system 16 may comprise a bracket that may be fitted onto the ultrasound transducer. In particular embodiments, the out-of-plane needle guidance system 16 may utilize a plurality of tabs, where each tab corresponds to a particular needle gauge, or a particular depth sought by the operator. In particular embodiments, an operator may choose a tab suitable for a particular procedure, remove it from the plurality of tabs, and snap the tab onto the bracket, forming a guide at the desired target depth. In particular embodiments, the out-of-plane needle guide may further include a quick-release system to allow the needle to be removed. In particular embodiments, once the needle is removed, the chosen tab may also be removed and disposed of.

In particular embodiments, the mechanical play between a needle 15 and an out-of-plane needle guidance system 16 may be up to 1.5 degrees, meaning that the angular variation of the needle with respect to its intended trajectory may be as much as 1.5 degrees. In particular embodiments, given this uncertainty in the angle of the needle, the potential magnitude of the displacement of the needle from the projected point may increase the deeper the needle travels. In particular embodiments, the amount of mechanical play may be known based on the needle used and the particular tabs used for that needle. As an example and not by way of limitation, it may be already known that for a particular needle, the tab for a depth of 1 cm may allow the needle to move by 0.5 degrees, while the tab for a depth of 2.5 cm may allow the needle to move by as much as 1.0 degree.

Figure 2:
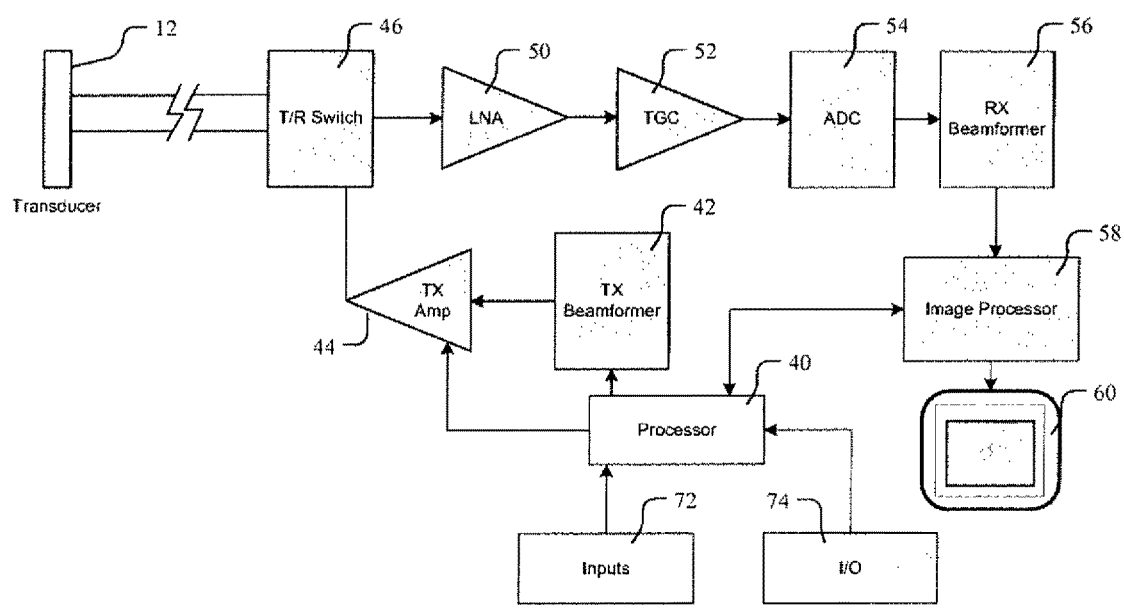
FIG. 2 depicts a block diagram of an example ultrasound imaging system for out-of-plane needle guidance.

FIG. 2 depicts a simplified block diagram of an ultrasound imaging system in accordance with an embodiment of the disclosed technology. In particular embodiments, the ultrasound system may be constructed with components that are different than those shown. In addition, the ultrasound system may include parts that are not discussed (e.g. a power supply etc.) and that are not necessary for the understanding of how to make and use the disclosed technology. In the embodiment shown, the ultrasound system may include a processor 40 having a built-in or external memory (not shown) containing instructions that are executable by the processor to operate the ultrasound imaging system as will be explained in detail below. In the transmit path, the ultrasound system may include a transmit beamformer 42, a transmit gain control amplifier 44 and a transmit/receive switch 46. If the ultrasound transducer 12, is a phased array type or can otherwise change the angle of transmissions electronically, the transmit beamformer 42 may operate to generate a number of signals having a relative amplitude and phase (timing) that are selected to produce an ultrasound beam from some or all of the transducer elements of the transducer that constructively add in a desired transmit beam direction (the desired transmit beam angle). The signals from the transmit beamformer may be amplified by the transmit amplifier 44 to a sufficiently high voltage level that will cause the transducer elements to produce the desired acoustic signals in the tissue being examined. In particular embodiments, the processor 40 may be connected to supply a control command such as a digital value (e.g. 0-255) to the gain control amplifier. The value of the command may control the amount of gain that is supplied by the transmit amplifier 44.

Other techniques for adjusting the power of the ultrasound signals may include changing the waveforms that drive the transducer elements to either increase or decrease the power of the ultrasound signals. In particular embodiments, the voltage rails (+V, −V) of an amplifier that produces the driving signals may be changed in order to vary the power of the ultrasound signals. In particular embodiments, driving signals may be supplied to a lesser or a greater number of transducer elements to change the power of the ultrasound signals. Those skilled in art may understand that these techniques are merely exemplary and that there may be numerous ways in which the level of acoustic power of the ultrasound signals delivered to the patient can be adjusted.

In particular embodiments, the amplified transmit signals may be supplied to the transducer 12 through the transmit/receive switch 46, which disconnects or shields sensitive receive electronics from the transmit signals at the time they are delivered to the transducer 12. After the signals are transmitted, the transmit/receive switch 46 may connect the receive electronics to the transducer elements to detect the corresponding electronic echo signals created when the returning acoustic waves impinge upon the transducer elements.

In particular embodiments, in the receive path, the ultrasound imaging system may include a low noise amplifier 50, a time gain control (TGC) amplifier 52, an analog to digital converter 54, a receive beamformer 56 and an image processor 58. Analog echo signals produced by the imaging transducer may be directed through the transmit/receive switch 46 to the low noise amplifier where they are amplified. The TGC amplifier 52 may apply a variable amplification to the received signals that varies the level of amplification applied with the return time of the signals (e.g. proportional to the depth in the tissue being imaged) to counteract the attenuation of the signals versus depth. The amplified signals may then be converted into a digital format by the analog to digital converter 54. The digitized echo signals may then be delayed and summed by the receive beamformer 56 before being supplied to the image processor.

In particular embodiments, the number of transmitted beams and received beams (lines) may differ from each other. As an example and not by way of limitation, the receive beamformer may produce in parallel (i.e., simultaneously) two or more adjacent lines per transmitted beam, a technique sometimes known as parallel receive beamforming or multi-line processing. Multi-line processing may be used to increase the imaging frame rate by lowering the number of transmitted beams while still being able to keep the number of received lines per frame (line density) constant. In particular embodiments, a higher multi-line order (number of receive lines beamformed in parallel from a single transmitted beam) may be used to increase the number of received lines per frame while keeping the number of transmitted beams, hence the frame rate, constant. Other combinations of line density, frame rate and multi-line order may also be possible. Furthermore, it may be possible to transmit an unfocused beam (plane wave) and beamform all the receive lines of a frame from that single transmitted beam. The system may also employ different combinations of line density and multi-line order for imaging the tissue vs. imaging an interventional instrument. In particular embodiments, use of a higher multi-line order, a lower-line density, or unfocused transmit beams, while improving the frame rate, may reduce the quality of the acquired images.

Images produced by the image processor 58 from the received signals may be displayed on a display 60. In addition, the images may be recorded in an image memory (not shown) for future recall and review. A number of inputs 72 may be provided to allow an operator to change various operating parameters of the ultrasound imaging system and to enter data such as the patient's name or other record keeping data. In addition, the ultrasound imaging system may include input/output (I/O) circuitry to allow the system to connect to computer communication links (LAN, WAN, Internet etc.) through a wired (e.g. Ethernet, USB, Thunderbolt, Firewire, or the like) or wireless (802.11, cellular, satellite, BLUETOOTH® or the like) communication link.

The details of the components that comprise the ultrasound imaging system and how they operate may be generally considered to be well known to those of ordinary skill in the art. Although the ultrasound imaging system is shown having many separate components, devices such as ASICs, FPGAs, digital signal processors (DSPs), CPUs or GPUs may be used to perform the function of multiple ones of these individual components.

As discussed above, the processor 40 may be programmed to create a composite image of the tissue being examined and a needle being introduced into the tissue. In particular embodiments, the image processor may produce an anatomy image of the tissue being examined with imaging parameters that are selected for the depth and particular type of tissue being scanned. The anatomy image created by the image processor 58 may be stored in memory to be combined with echo data for one or more of the needle frames that are created to locate an interventional instrument.

FIGS. 3A-3B depict an example embodiment of existing on-screen depth markers for out-of-plane needle guidance systems. In the example of FIG. 3A, the ultrasound image 300 may depict the anatomic structure 310 of interest, while a needle is to be inserted into the anatomic structure 310 from a direction orthogonal to the plane of ultrasound image 300. In the example of FIG. 3, the ultrasound imaging system may further display a set of on-screen depth markers 321-325, each of which correspond to a particular location where the needle may intersect the ultrasound plane, for a given depth of the needle. As an example and not by way of limitation, depth marker 321 may correspond to a depth of 0.5 cm, depth marker 322 may correspond to 1.0 cm, depth marker 323 may correspond to 1.5 cm, depth marker 324 may correspond to 2.0 cm, and depth marker 325 may correspond to 2.5 cm. In the example of FIG. 3, depth markers 322 and 324 appear larger than depth markers 321, 323, and 325, for the operator's benefit in distinguishing the series of depth markers. In particular embodiments, the depth markers may be accompanied by a numerical value indicating the depth corresponding to each depth marker. In particular embodiments, the depth markers 321-325 may be automatically generated by the ultrasound imaging system based on an indication by the operator that the operator wishes to perform an out-of-plane needle insertion procedure, with the depths for each depth marker 321-325 automatically set by the ultrasound imaging system. In particular embodiments, the operator may select one or more depth markers to display and one or more depth makers to not display. As an example and not by way of limitation, if the operator knows that he or she is attempting an out-of-plane needle insertion at a depth of 2.0 cm, the operator may manually select only depth marker 324 to be displayed, while depth markers 321-323 and 325 are not displayed. This may reduce clutter on the ultrasound image and make the ultrasound image 300 clearer to the operator to avoid confusion.

FIG. 3B depicts the ultrasound image used in the example of FIG. 3A, but with a visualization of a needle 24 intersecting the plane of the ultrasound image 300. In the example of FIG. 3B, continuing the example discussed above for FIG. 3A, the operator may have selected a needle guide and needle appropriate for a depth of 1.5 cm, corresponding to depth marker 323. In particular embodiments, the ultrasound imaging system may use known methods of automatically detecting a needle in an ultrasound image to determine that a needle is now present in the example ultrasound image 300 of FIG. 3B. In particular embodiments, the operator may provide a further input to the ultrasound imaging system when he or she perceives the needle on the ultrasound image 300. In particular embodiments, when the needle is detected, either automatically or by the operator, the ultrasound imaging system may remove the on-screen depth markers 321-325, or otherwise reduce their visibility on the ultrasound image 300, for example, by making one or more of the on-screen-depth markers 321-325 more transparent. In the example of FIG. 3B, the needle 24 is displaced by a small amount from the on-screen depth marker 323 corresponding to the intended depth and target. In particular embodiments, the displacement may be due to a number of factors including but not limited to needle deflection, mechanical play between the needle and the needle guide or the needle guide and the ultrasound transducer, or tissue density. The example of FIG. 3B may highlight a potential downside to only using on-screen depth markers for target depths, where for any of a number of reasons, the needle may diverge from the predicted location.

In particular embodiments the ultrasound imaging system may be configured to calculate the probability that an out-of-plane needle insertion will intersect the plane of the ultrasound image at particular areas. Multiple factors may influence the probability of intersection. For example, the mechanical play between the needle and the guidance system, as discussed above, may contribute uncertainty based on the angle of freedom that the needle has. Other factors that may affect the trajectory of the needle and may be used as input by the ultrasound imaging system may include the fit of the bracket on the transducer housing, the alignment of the transducer array within the transducer housing, potential deflection of the needle as it progresses through tissue, physical properties of the needle, the depth of the needle placement, the elevation profile of the ultrasound beam, and the tissue density. In particular embodiments, one or more of these factors may be combined by the ultrasound imaging system to determine a high-confidence area in the ultrasound image where the likelihood that the needle will intersect within the high-confidence area is above a threshold. In particular embodiments the probability threshold can be above 85%, 90%, 95%, 99%, or 99.9% probability of intersection. As an example and not by way of limitation, the ultrasound imaging system may determine a high-confidence area having a 99% likelihood that the needle will intersect the ultrasound image plane through a point within the high-confidence area.

In particular embodiments, the tissue density and the deflection of the needle may impact the trajectory of the needle and have compounding effects. As an example and not by way of limitation, the tissue density may affect the amount of deflection that the needle may have as it progresses through tissue. A needle being inserted through muscle tissue may be affected by more resistance than a needle being inserted through lipid tissue, and thus the needle going through a muscle may incur a greater amount of deflection. Furthermore, in particular embodiments, shallower target depths may utilize a thinner needle, while deeper target depths may correspond to a thicker needle. In particular embodiments, the tissue density may also affect the accuracy of the ultrasound image relative to the needle. Different types of tissue may have different densities and water content, and even the same type of tissue (for example, muscles) may have varying densities and water content based on the patient, the location of the tissue in the patient's body, the time of day, the patient's hydration levels, etc. These factors may affect the accuracy of the ultrasound imaging system's ability to accurately render an ultrasound image, since ultrasound imaging systems use a consistent speed of sound through the medium for the propagation of the ultrasound pulses through the anatomic structure. This may be noticeable in ultrasound images that depict two distinct anatomic structures, such as muscle tissue right next to a bone. In particular embodiments, an ultrasound imaging system may be able to adjust its imaging settings to account for the tissue density of one or more of the anatomic structures featured in the ultrasound image. In particular embodiments, for example, when using a 3D or biplane transducer, the ultrasound imaging system may be able to determine, based on any displacement of the needle visualization from the expected location based on the tissue density, whether the tissue is different from what was assumed for the imaging, or if the water content in the tissue is abnormal. As an example and not by way of limitation, if the patient is dehydrated, his or her tissue density may be different from what would be expected, which may affect the final location of the needle relative to the anticipated target area.

In particular embodiments, the ultrasound imaging system may leverage other algorithms that will detect whether the target area in the anatomic structure is within the high-confidence area prior to and during the needle insertion procedure. As an example and not by way of limitation, an operator may be able to indicate on the ultrasound system, prior to any needle insertion, both the target depth for a needle, as well as the anatomic feature being targeted at that depth, such as a blood vessel. Once the ultrasound imaging system has received the selection of what type of needle is used the corresponding depth, and what the target feature is, it may determine on a real-time or near-real-time basis whether the target feature encompasses most if not all of the high-confidence area, to ensure that the needle may not miss the target area altogether. Prior to the procedure, the ultrasound imaging system may determine based on the needle to be used and the target area whether the needle insertion procedure as set up will successfully place the needle in the target area, and notify the operator that he or she should proceed. In particular embodiments, if the ultrasound imaging system determines that the high-confidence area does not overlap with the target area sufficiently to ensure that the needle reaches the target area, the ultrasound imaging system may inform the operator that he or she should shift the position of the patient, the ultrasound transducer, or use a different needle and/or needle guide. In particular embodiments, once the needle insertion process commences, the position of the needle or the target area may shift, such as due to the subject person moving. If the ultrasound imaging system determines during the insertion process, but prior to the needle intersecting the ultrasound image plane, that the needle will miss the target area, the ultrasound imaging system may notify the operator that the procedure may not succeed, and allow the operator to reset the procedure and try again before the needle is fully inserted.

FIG. 4A depicts the relationship between needle insertion angle and the ultrasound image plane. In the view of FIG. 4A, the needle 15 may be inserted from a location to the left of the plane of the ultrasound image 300, with the trajectory of the needle going down and to the right. Based on the tab used with the needle guidance system, the needle 15 will follow one of the marked trajectories towards the high-confidence areas 421A-425A. In the example of FIG. 4A, for each possible trajectory, the ultrasound imaging system may determine that the needle will shift by two degrees or less from the projected path.

FIG. 4B provides the projection of the calculated trajectories of needle 15 to high-confidence areas 421A-425A as they cross the plane for the ultrasound image 300. In the example of FIG. 4B, the high-confidence areas 421A-425A are larger as the depth increases, due to the greater potential displacement for needles that have to travel further to reach the ultrasound image plane 300. Other factors affecting the trajectory of the needle, described hereinabove, can also affect the size of the high-confidence areas. Additionally, in the example of FIG. 4B, it can be seen that the high-confidence areas 421A-425B are narrower relative to each marker's height. In particular embodiments, this may reflect the determination that there is more mechanical play in a first direction than a second direction. In the example of FIGS. 4A and 4B, the high-confidence areas may have a threshold of 99%. In particular embodiments, the high-confidence area may be symmetric on all sides. For example, and not by way of limitation, the imaging system may determine that the needle may shift by two degrees or less in any direction. In particular embodiments, the high-confidence area may be asymmetric. As an example and not by way of limitation, the imaging system may determine that the needle may shift by two degrees in a first direction but only one degree in a second direction. As another example and not by way of limitation, the high-confidence level may not be centered on the exact predicted pathway, because there is a greater chance that the needle will shift to one direction based on the factors described above.

In particular embodiments, the ultrasound imaging system may be configured to display one or more on-screen markers on an ultrasound image that correspond to a high-confidence area or areas. The size, shape, opacity, and other features of the on-screen markers can be based on the high-confidence area, for example, the size, shape, or threshold of the high-confidence area. In particular embodiments, the on-screen markers may be shaped asymmetrically to indicate a high-confidence area that is not symmetrical in either the vertical or lateral direction, due to the factors that may impact the accuracy of the imaging and the needle placement, as discussed above. In particular embodiments, the size, shape, or other features of the on-screen marks can be changed dynamically before and during a needle-insertion procedure. For example, the ultrasound imaging system may continue to determine and adjust the high-confidence areas during the procedure, and the on-screen markers can be dynamically changed. As an example, and not by way of limitation, as the needle moves closer to a target, the threshold of a high-confidence area may increase, and the size, shape, or color of the corresponding on-screen marker can be adjusted accordingly.

Figure 4C:
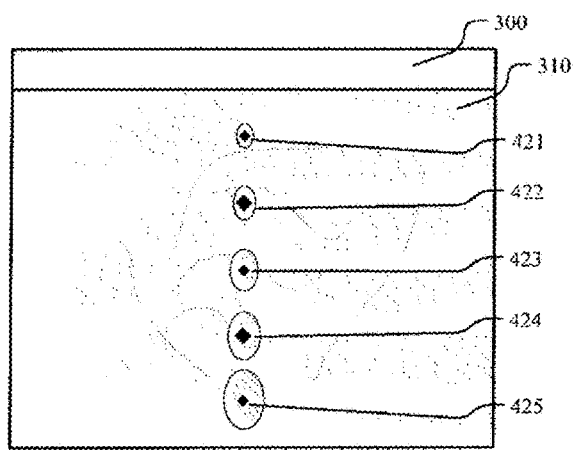

FIG. 4C depicts an example view of an ultrasound image 300 with on-screen markers 421-425 corresponding with high-confidence areas 421A-425A, respectively. As with FIGS. 3A and 3B, the ultrasound image 300 depicts the anatomic structure 310 being imaged. In addition to the depth markers shown in FIGS. 3A and 3B, the ultrasound image 300 of FIG. 4C uses on-screen markers 421-425, which correspond with high-confidence areas 421A-425A, respectively. In the example of FIG. 4C, each on-screen marker may corresponds with high-confidence areas 421-425A each having a threshold of 99%.

Figure 4D:
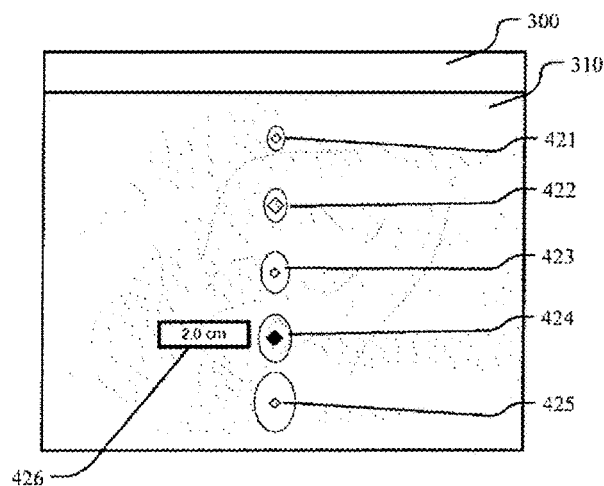

FIG. 4D depicts another example view of on-screen markers for the high-confidence levels for needle placement. For the example of FIG. 4D, it may be desirable that the operator remove some of the visual clutter that may be present in the example of 4C, where all five determined on-screen markers are visible in the ultrasound image 300. In the example of FIG. 4D, the operator may select a single on-screen marker to be displayed, based on the selected needle and needle guide. In response to this determination, the ultrasound imaging system may only prominently display the selected on-screen marker 424, for example, by using an inverse color of the ultrasound image. This can make on-screen marker 424 stand out without being overly obtrusive. The ultrasound imaging system may reduce the visibility of the other on-screen markers 421-423, 425. For example, markers 421-423, 425 can be presented with greater transparency, presented in grey scale, or otherwise differentiated from the ultrasound image. In particular embodiments, on-screen markers 421-423, 425 can be removed. In particular embodiments, the ultrasound imaging system may provide information about one or more of the displayed on-screen markers, such as the depth, threshold of the corresponding high-confidence area, the total area of the corresponding high-confidence area, or whether the needle has entered the corresponding high-confidence area. In particular embodiments, the information can be updated dynamically, for example, as the needle approaches and intersects (or misses) the high-confidence area. In the example of FIG. 4D, a notation 426 is present for the selected on-screen marker 424 showing the depth for on-screen marker 424. In particular embodiments, information may be automatically displayed in the ultrasound image 300. In particular embodiments, the operator may provide input specifying information that is to be displayed.

In particular embodiments, the ultrasound imaging system may determine multiple high-confidence areas having different thresholds for a given depth to be depicted within corresponding on-screen markers. As an example and not by way of limitation, the ultrasound imaging system may use an on-screen marker having a first shade and corresponding with a high-confidence area having a 99% threshold, which is the largest area; a second shade on-screen marker corresponding with a high-confidence area having a 95% threshold, which will be slightly smaller; and a third shade on-screen marker corresponding with a high-confidence area having an 85% threshold, which is even smaller in size. In particular embodiments, using multiple confidence levels may show an operator if there are any particular risks of the needle missing the intended target or impinging on another anatomic feature. In particular embodiments, the ultrasound imaging system may automatically determine the number of thresholds to determine, and the values of each threshold (e.g., 99%, 95%, 90%). In particular embodiments, the operator may specify via user input how many thresholds, and what values, should be used for the imaging. As an example and not by way of limitation, if for a particular needle insertion it is imperative that the operator avoid the needle impinging on a nearby anatomic structure, the operator may increase the threshold required (e.g. to 99.9%) so that the operator may be more confident that he or she will avoid the nearby structure. With reference to FIG. 4E, for purpose of illustration and not limitation, the on-screen markers 431-435 may utilize different shades to indicate different confidence levels, with the smallest marked regions indicating lower confidence levels. For example, on-screen marker 435A corresponds with a high-confidence area having a threshold of 99%; on-screen marker 435B corresponds with a high-confidence area having a threshold of 95%; on-screen marker 435C corresponds with a high-confidence area having a threshold of 90%; on-screen marker 435A corresponds with a high-confidence area having a threshold of 85%. On-screen marker 435A is the largest and lightest of markers 435A-D and on-screen marker 435D is the smallest and darkest of markers 435A-D. As shown in the example of FIG. 4E, each smaller area reflecting a lower confidence level may not necessarily be concentric with the larger area for higher confidence levels, based on the factors used by the ultrasound imaging system.

FIG. 4F depicts another example view of on-screen markers 431-435 as with FIG. 4E. In the example of FIG. 4F, the operator is able to select a single on-screen marker 432, indicating that the operator intends to insert a needle at a depth corresponding to on-screen marker 432. In this example, the ultrasound imaging system may change the ultrasound image 300 to reduce the visibility of the unselected on-screen markers 431 and 433-435. In addition, ultrasound image 300 may add a picture-in-picture 440 of the selected on-screen marker 432 and the surrounding tissue, so that the operator is provided with a close-up view of the region where the needle is expected to intersect the image. In particular embodiments, the ultrasound imaging system may opt for only reducing visibility of the unselected on-screen markers, or only providing the picture-in-picture 440.

Figure 4G:
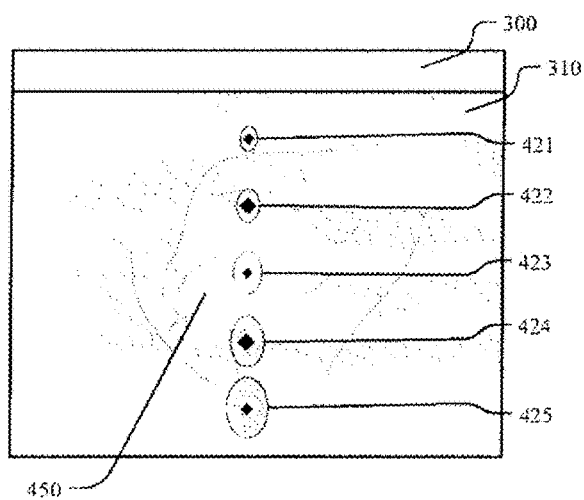

FIG. 4G depicts another example view of on-screen markers 421-425, as with FIGS. 4C and 4D. In the example of FIG. 4G, the operator may select on-screen marker 423 as the target for the out-of-plane needle procedure. In this example, the ultrasound imaging system may then select an area 450 around on-screen marker 423, and change the image processing parameters in area 450 to make it visually distinctive to the operator. As an example and not by way of limitation, area 450 may be displayed with a greater contrast, different color hues, or other methods of enhancing the visibility of area 450 to the rest of ultrasound image 300. In particular embodiments, the screen may be updated automatically based on dynamic calculations of the high-confidence areas.

Figure 4H:
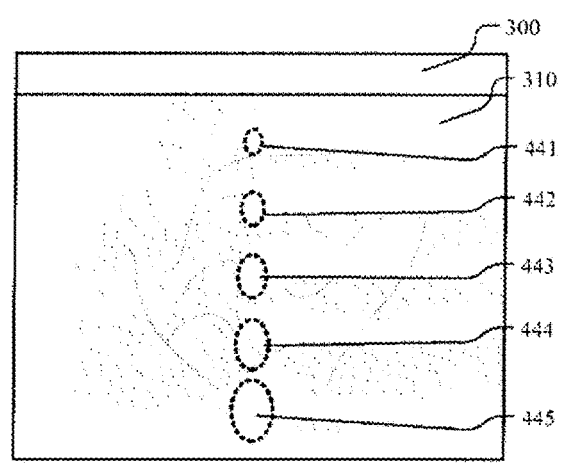

FIG. 4H depicts another example view of on-screen markers 441-445. In this example, the on-screen markers are simply a loop corresponding with an outline of the high-confidence areas. In particular embodiments, using on-screen markers 441-445 may show the operator where the needle is expected to emerge, without adding more clutter to the details of the ultrasound image 300.

Figure 5:
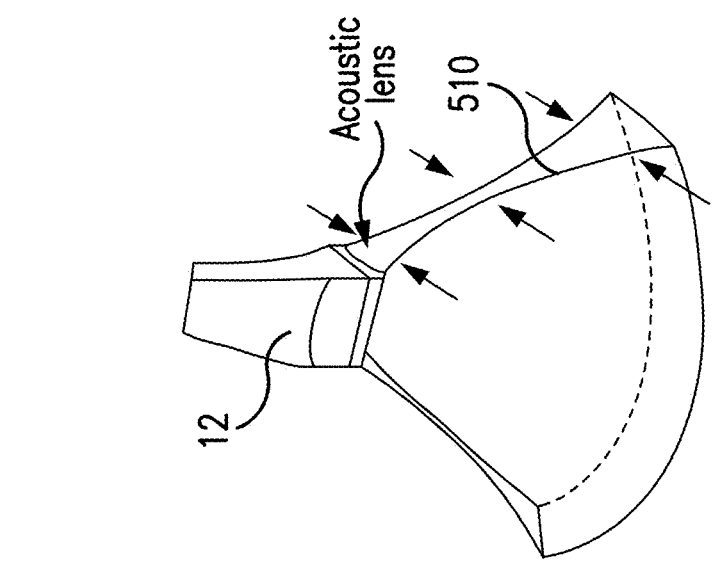
FIG. 5 depicts an example elevation profile of an ultrasound beam relative to the transducer.

In particular embodiments, the determination of the high-confidence areas may be based on the shape of the ultrasound beam as a function of depth. FIG. 5 depicts an example ultrasound beam formed by a focused ultrasound transducer 12, forming an elevation profile 510. As shown in the example of FIG. 5, the elevation profile 510 reflects an initial broad region roughly corresponding to the aperture size of the transducer, then narrows over an initial distance, then eventually broadens again. In particular embodiments, because the thickness of the ultrasound image may vary with depth, the determination of the on-screen markers may also shift. It would be understood in the art that the elevation profile of the beam over depth (i.e. distance from the transducer) may be predicted from the diameter of the transducer face and the wavelength used. In particular embodiments, because the elevation profile of the beam changes with depth, the thickness of the view represented in an ultrasound image may not be consistent throughout the image.

Figure 6B:
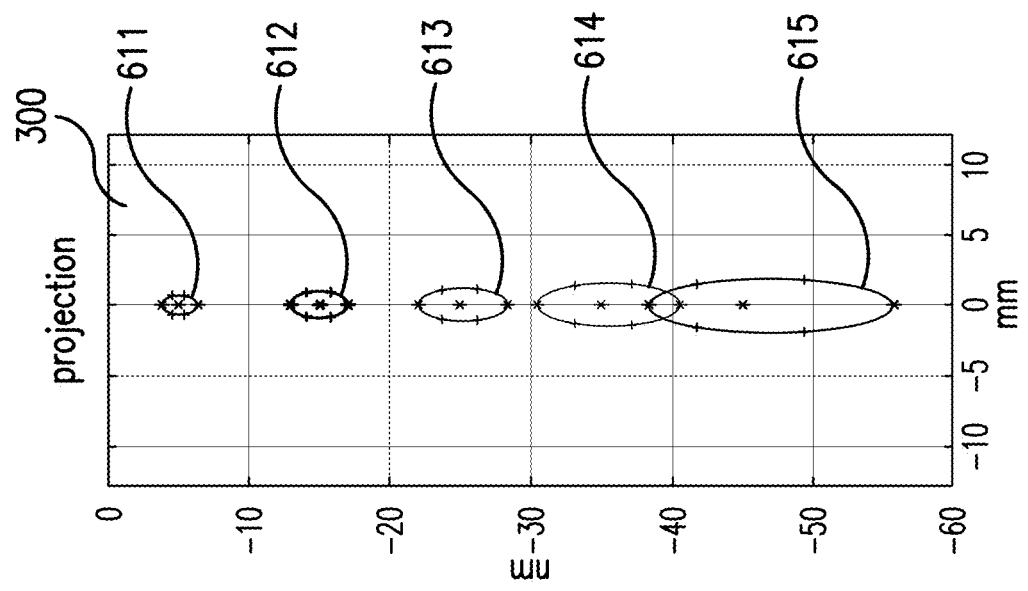
FIGS. 6A-6B depict the relationship between needle insertion angle and an elevation profile of the of the ultrasound image plane.
Figure 6A:
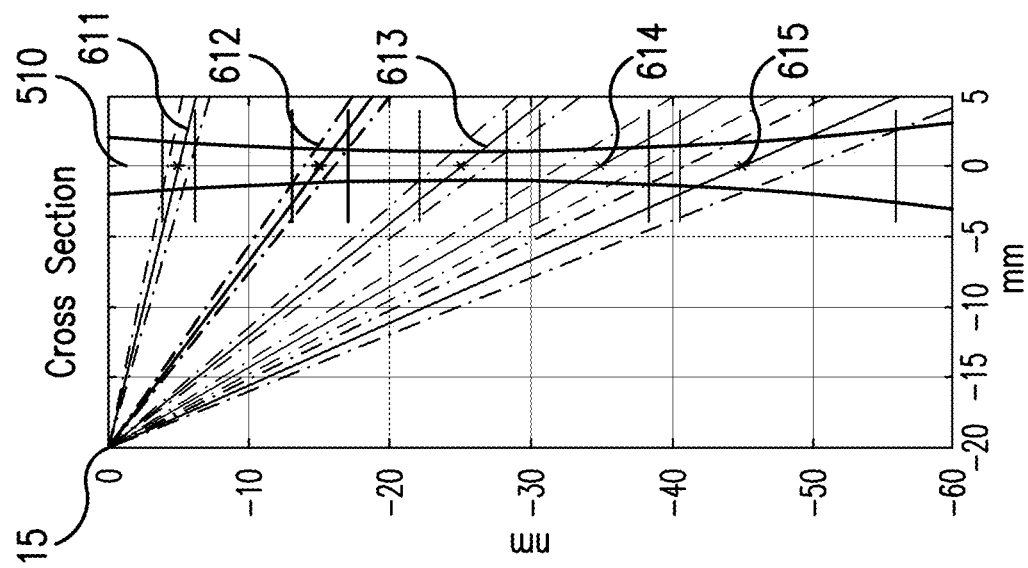

FIG. 6A depicts the relationship between needle insertion angle and the ultrasound imaging plane of a beam having an elevation profile 510. FIG. 6B provides the projection of the calculated trajectories of needle 15 to high-confidence areas 611-615. Similar to FIG. 4A, in the example of FIG. 6A, the needle 15 is being inserted from the left and from the top of FIG. 6A, with the ultrasound image plane depicted by the elevation profile 510 as shown in FIG. 5. For the example of FIG. 6A, the elevation thickness 510 is plotted as a parabolic arc. In FIG. 6A, the trajectories for the needle 15 are plotted as on-screen markers 611-615, based on the same potential angular shift as shown for FIG. 4A. However, the variable thickness along the elevation profile 510 can affect the size of the high-confidence areas 611-615. In particular, as the depth increases and the thickness of the beam increases, the shapes of the high-confidence areas 614 and 615 may be difference compared to calculations using a beam having a constant thickness (for example as shown in FIGS. 4A-4B).

Figure 7:
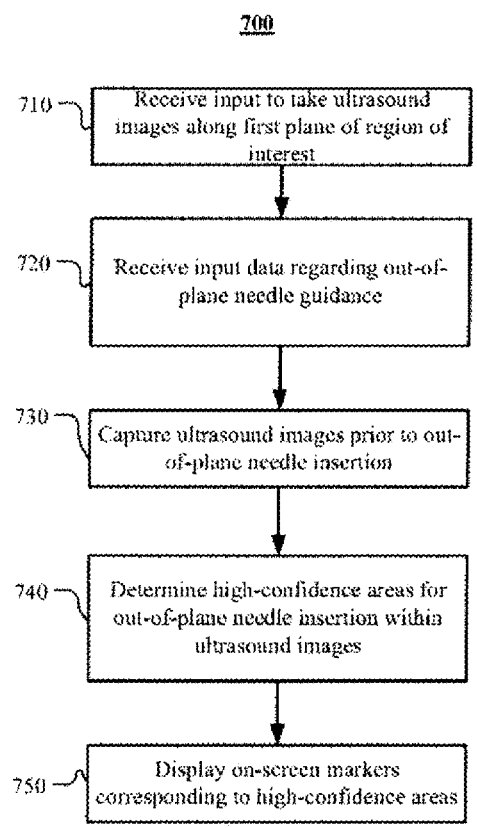
FIG. 7 depicts an example method for displaying on-screen markers on an ultrasound imaging system, the on-screen markers corresponding to areas having a high-confidence that an out-of-plane needle will intersect the ultrasound image.

FIG. 7 depicts an example method 700 for displaying on-screen markers on an ultrasound imaging system, the on-screen markers corresponding to areas having a high-confidence that an out-of-plane needle will intersect the ultrasound image. At step 710, the ultrasound imaging system may receive an indication to take ultrasound images along a first plane of a region of interest. As an example and not by way of limitation, the region of interest may be an anatomic structure with a target region for needle insertion. At step 720, the ultrasound imaging system may further receive input that an out-of-plane needle insertion process will take place for the ultrasound images along the first plane. As an example and not by way of limitation, the operator of the ultrasound imaging system may affix an out-of-plane needle guidance system to an ultrasound transducer, and select and attach a tab appropriate for the needle used and the desired target depth. The needle insertion may take place along a second plane that is orthogonal to the first plane. At step 730, the ultrasound imaging system may initiate capture of ultrasound images of the region of interest along the first plane. At step 740, the ultrasound imaging system may determine one or more high-confidence areas for where an inserted needle may intersect the first plane. The determining may be based on the ultrasound image and information regarding the out of plane needle insertion. At step 750, the ultrasound imaging system may display one or more on-screen markers corresponding to the one or more high-confidence areas in conjunction with the plurality of ultrasound images on the display.

Particular embodiments may repeat one or more steps disclosed in FIG. 7, where appropriate. Although this disclosure describes and illustrates particular steps of the method of FIG. 7 as occurring in a particular order, this disclosure contemplates any suitable steps of the method of FIG. 7 occurring in any suitable order. Moreover, although this disclosure describes and illustrates particular components, devices, or systems carrying out particular steps of the method of FIG. 7, this disclosure contemplates any suitable combination of any suitable components, devices, or systems carrying out any suitable steps of the method of FIG. 7.

In particular embodiments, the present invention utilizing on-screen markers for out-of-plane needle guidance based on confidence levels may offer an advantage over previous on-screen markers for out-of-plane needle guidance by providing additional feedback to the operator on not only where the needle should intersect the ultrasound image plane, but also where it could intersect. In particular embodiments, this may allow operators to adjust the needle guide or the ultrasound transducer's positioning relative to the anatomic structure prior to insertion of the needle to ensure that the needle will intersect the targeted structure, or ensure that the needle will likely avoid intersecting a different structure.

The subject matter and the operations described in this specification may be implemented in digital electronic circuitry, or in computer software, firmware, or hardware, including the structures disclosed in this specification and their structural equivalents, or in combinations of one or more of them. Embodiments of the subject matter described in this specification may be implemented as one or more computer programs, i.e., one or more modules of computer program instructions, encoded on computer storage medium for execution by, or to control the operation of, data processing apparatus.

A computer storage medium may be, or may be included in, a computer-readable storage device, a computer-readable storage substrate, a random or serial access memory array or device, or a combination of one or more of them. Moreover, while a computer storage medium is not a propagated signal, a computer storage medium may be a source or destination of computer program instructions encoded in an artificially-generated propagated signal. The computer storage medium also may be, or may be included in, one or more separate physical components or media (e.g., multiple CDs, disks, or other storage devices).

The term "processor" encompasses all kinds of apparatus, devices, and machines for processing data, including by way of example a programmable processor, a computer, a system on a chip, or multiple ones, or combinations, of the foregoing. The apparatus may include special purpose logic circuitry, e.g., an FPGA (field programmable gate array) or an ASIC (application-specific integrated circuit). The apparatus also may include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment may realize various different computing model infrastructures, such as web services, distributed computing and grid computing infrastructures.

A computer program (also known as a program, software, software application, script, or code) may be written in any form of programming language, including compiled or interpreted languages, declarative or procedural languages, and it may be deployed in any form, including as a stand-alone program or as a module, component, subroutine, object, or other unit suitable for use in a computing environment. A computer program may, but need not, correspond to a file in a file system. A program may be stored in a portion of a file that holds other programs or data (e.g., one or more scripts stored in a markup language document), in a single file dedicated to the program in question, or in multiple coordinated files (e.g., files that store one or more modules, sub-programs, or portions of code). A computer program may be deployed to be executed on one computer or on multiple computers that are located at one site or distributed across multiple sites and interconnected by a communication network.

The processes and logic flows described in this specification may be performed by one or more programmable processors executing one or more computer programs to perform actions by operating on input data and generating output. The processes and logic flows may also be performed by, and apparatus can also be implemented as, special purpose logic circuitry, e.g., an FPGA (field programmable gate array) or an ASIC (application-specific integrated circuit).

Processors suitable for the execution of a computer program may include, by way of example and not by way of limitation, both general and special purpose microprocessors. Devices suitable for storing computer program instructions and data may include all forms of non-volatile memory, media and memory devices, including by way of example but not by way of limitation, semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory may be supplemented by, or incorporated in, special purpose logic circuitry.

From the foregoing, it may be appreciated that specific embodiments of the invention have been described herein for purposes of illustration, but that various modifications may be made without deviating from the scope of the invention. Accordingly, the invention is not limited except as by the appended claims.

What is claimed is:

1. An ultrasound imaging system comprising an image processor configured to:
   receive input data for capturing ultrasound images of a region of interest along a first plane, the input data including an indication that an interventional instrument will be inserted along a second plane into the region of interest, the second plane being orthogonal to the first plane;
   capture the ultrasound images sequentially along the first plane;
   calculate, for a respective particular area of a plurality of particular areas, a probability that the interventional instrument, when inserted along the second plane, will intersect the first plane at the respective particular area;
   determine one or more high-confidence areas within the region of interest where the interventional instrument will intersect the first plane based on the probability being above a threshold;
   display at least one ultrasound image of the ultrasound images and one or more on-screen markers corresponding to the one or more high-confidence areas;
   detect that the interventional instrument has intersected the first plane;
   provide an indication on the at least one displayed ultrasound image of a location of the interventional instrument within the first plane; and
   automatically remove the one or more on-screen markers from the at least one displayed ultrasound image when the interventional instrument is detected to have intersected the first plane.

2. The ultrasound imaging system of claim 1, wherein the interventional instrument is inserted along the second plane via a guidance system, the guidance system being affixed to an ultrasound transducer of the ultrasound imaging system.

3. The ultrasound imaging system of claim 1, wherein each of the one or more high-confidence areas corresponds respectively to a particular depth within the region of interest from an ultrasound transducer of the ultrasound imaging system.

4. The ultrasound imaging system of claim 1, wherein the determination of the one or more high-confidence areas is further based on calculating a potential deflection of the interventional instrument during insertion based at least on one of a density of tissue or physical properties of the interventional instrument.

5. The ultrasound imaging system of claim 1, wherein:
   the ultrasound images along the first plane comprise an elevation thickness that varies as a function of depth; and
   the determination of the one or more high-confidence areas is further based on the elevation thickness at each high-confidence area within the ultrasound images.

6. The ultrasound imaging system of claim 1, wherein the image processor is further configured to:

receive input data indicating a target within the region of interest;
determine whether a high-confidence area overlaps the target; and
notify an operator of the ultrasound imaging system whether the high-confidence area overlaps the target.

7. The ultrasound imaging system of claim 6, wherein the image processor is further configured to:
determine that the interventional instrument is being inserted into the region of interest along the second plane;
determine whether the high-confidence area remains overlapping with the target; and
in response to determining that the high-confidence area no longer overlaps the target, notify the operator that the high-confidence area does not overlap the target.

8. The ultrasound imaging system of claim 1, wherein the image processor is further configured to:
receive a selection of a single on-screen marker from the one or more on-screen markers; and
remove at least one unselected on-screen marker of the one or more on-screen markers from the ultrasound images.

9. The ultrasound imaging system of claim 1, wherein the image processor is further configured to:
receive a selection of at least one selected on-screen markers from the one or more on-screen markers; and
modify a color of the at least one selected on-screen markers.

10. The ultrasound imaging system of claim 1, wherein the image processor is further configured to:
receive a selection of at least one selected on-screen markers from the one or more on-screen markers; and
display the at least one selected on-screen marker in a picture-in-picture on the display.

11. The ultrasound imaging system of claim 1, wherein the image processor is further configured to:
receive input data indicating a target within the region of interest;
prior to the interventional instrument being inserted, determine whether at least one of the one or more high-confidence areas overlaps the target;
notify an operator of the ultrasound imaging system that none of the one or more high-confidence areas overlaps the target; and
inform the operator that the operator should at least one of:
shift a position of a patient;
shift a position of an ultrasound transducer of the ultrasound imaging system;
use a different interventional instrument; or
use a different guide for the interventional instrument.

12. One or more computer-readable non-transitory storage media embodying software operable when executed by one or more computing devices of an ultrasound imaging system to perform one or more operations comprising:
receiving input data for capturing ultrasound images of a region of interest along a first plane, the input data including an indication that an interventional instrument will be inserted along a second plane into the region of interest, the second plane being orthogonal to the first plane;
capturing the ultrasound images sequentially along the first plane;
calculating, for a respective particular area of a plurality of particular areas, a probability that the interventional instrument will intersect the respective particular area;
determining one or more high-confidence areas of the region of interest where the interventional instrument will intersect the first plane based on the probability being above a threshold;
displaying at least one ultrasound image of the ultrasound images and one or more on-screen markers corresponding to the one or more high-confidence areas;
detecting that the interventional instrument has intersected the first plane;
providing an indication on the at least one displayed ultrasound image of a location of the interventional instrument within the first plane; and
automatically removing the one or more on-screen markers from the at least one displayed ultrasound image when the interventional instrument is detected to have intersected the first plane.

13. The storage media of claim 12, wherein the interventional instrument is inserted along the second plane via a guidance system, the guidance system being affixed to an ultrasound transducer of the ultrasound imaging system.

14. The storage media of claim 12, wherein each of the one or more high-confidence areas corresponds respectively to a particular depth within the region of interest from an ultrasound transducer of the ultrasound imaging system.

15. The storage media of claim 12, wherein the determining of the one or more high-confidence areas is further based on calculating a potential deflection of the interventional instrument during insertion based at least on a density of tissue or a physical property of the interventional instrument.

16. The storage media of claim 12 wherein:
the ultrasound images along the first plane comprise an elevation thickness that varies as a function of depth; and
the determining of the one or more high-confidence areas is further based on the elevation thickness at each high-confidence area within the ultrasound images.

17. The storage media of claim 12, wherein the operations further comprise:
receiving input data indicating a target within the region of interest;
prior to the interventional instrument being inserted, determining whether at least one of the one or more high-confidence areas overlaps the target;
notifying an operator of the ultrasound imaging system that none of the one or more high-confidence areas overlaps the target; and
informing the operator that the operator should perform at least one of:
shifting a position of a patient;
shifting a position of an ultrasound transducer of the ultrasound imaging system;
using a different interventional instrument; or
using a different guide for the interventional instrument.

18. A method comprising:
receiving input data for capturing ultrasound images of a region of interest along a first plane, the input data including an indication that an interventional instrument will be inserted along a second plane into the region of interest, the second plane being orthogonal to the first plane;
capturing the ultrasound images sequentially along the first plane;
calculating, based on the input data and the ultrasound images, a probability that the interventional instrument will intersect the first plane at a respective particular area of a plurality of particular areas;

determining one or more high-confidence areas of the region of interest where the interventional instrument will intersect the first plane based on the probability being above a threshold;

displaying at least one ultrasound image of the ultrasound images and one or more on-screen markers corresponding to the one or more high-confidence areas;

detecting that the interventional instrument has intersected the first plane;

providing an indication on the at least one displayed ultrasound image of a location of the interventional instrument within the first plane; and automatically removing the one or more on-screen markers from the at least one displayed ultrasound image when the interventional instrument is detected to have intersected the first plane.

19. The method of claim 18, wherein the interventional instrument is inserted along the second plane via a guidance system, the guidance system being affixed to an ultrasound transducer of the ultrasound imaging system.

20. The method of claim 18, wherein each of the one or more high-confidence areas corresponds respectively to a particular depth within the region of interest from an ultrasound transducer of the ultrasound imaging system.

* * * * *